Figure 1:
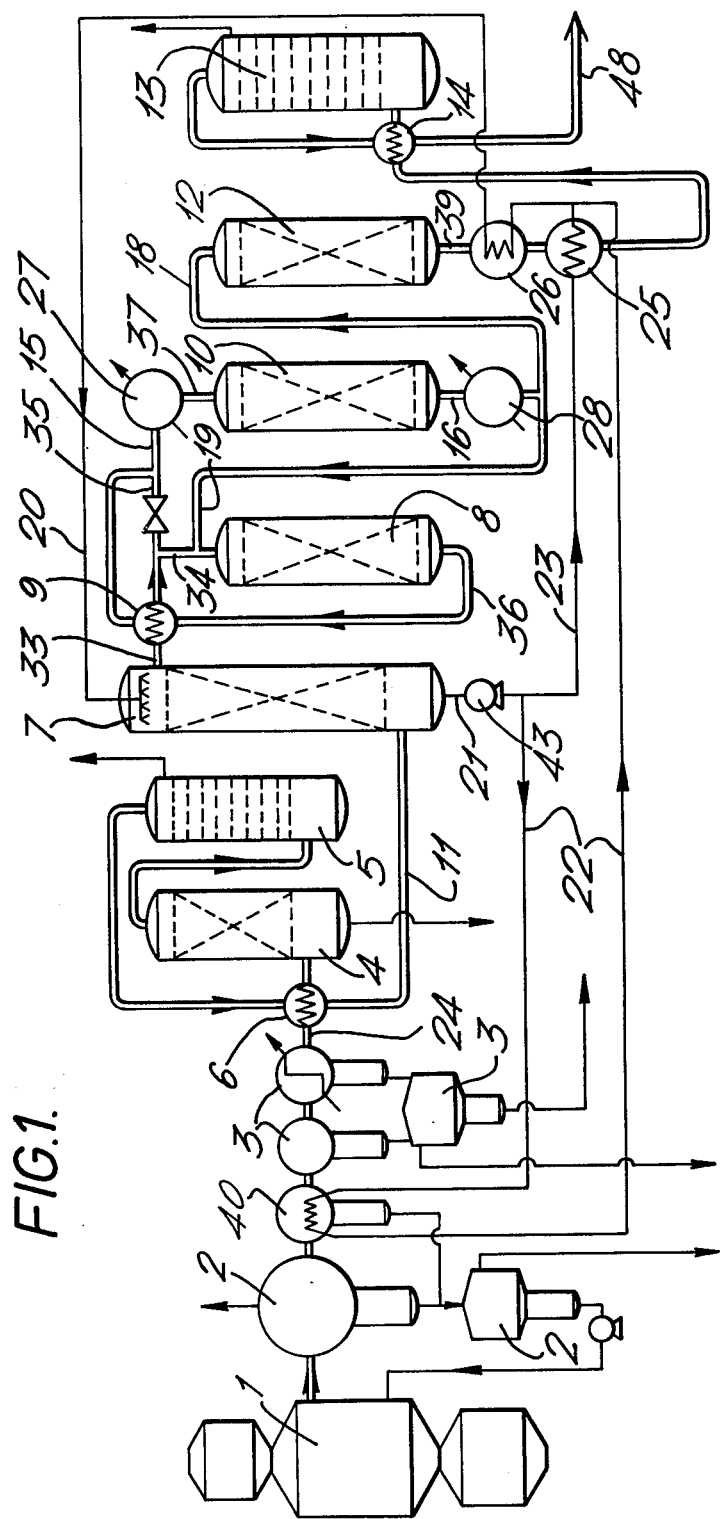

United States Patent [19]

Stroud et al.

[11] 4,133,825

[45] Jan. 9, 1979

[54] PRODUCTION OF SUBSTITUTE NATURAL GAS

[75] Inventors: Henry J. F. Stroud, Hockley Heath; Kenneth R. Tart, Dudley, both of England

[73] Assignee: British Gas Corporation, United Kingdom

[21] Appl. No.: 796,024

[22] Filed: May 11, 1977

[30] Foreign Application Priority Data

May 21, 1976 [GB] United Kingdom ............ 21086/76

[51] Int. Cl.² ................................................ C07C 27/06
[52] U.S. Cl. ............................ 260/449 M; 48/197 R
[58] Field of Search .................. 48/197 R; 260/449 M

[56] References Cited

U.S. PATENT DOCUMENTS

| | | | |
|---|---|---|---|
| 3,904,386 | 9/1975 | Graboski et al. | 260/449 M |
| 3,904,389 | 9/1975 | Banquy | 48/197 R |
| 3,930,812 | 1/1976 | Harris et al. | 48/197 R |
| 3,958,957 | 5/1976 | Koh et al. | 260/449 M |
| 3,967,936 | 7/1976 | Tajbl et al. | 48/197 R |
| 3,970,435 | 7/1976 | Schultz et al. | 48/197 R |
| 3,973,923 | 8/1976 | Staege et al. | 48/197 R |
| 4,005,996 | 2/1977 | Hausberger et al. | 48/197 R |

*Primary Examiner*—S. Leon Bashore
*Assistant Examiner*—George C. Yeung
*Attorney, Agent, or Firm*—Watson, Cole, Grindle & Watson

[57] ABSTRACT

Synthesis gases containing carbon monoxide, eg above 40% volume, and hydrogen are methanated to produce substitute natural gas, after $CO_2$ removal, wherein the synthesis gas is simultaneously saturated with water, further heated and divided into first and second feed gas streams. The first feed gas stream is catalytically methanated at a temperature of from 250 to 550° C, and the reaction product mixed with said second feed gas stream. The mixture is methanated over a second catalyst at a temperature of from 250 to 550° C and the product is divided into a second product gas stream and a recycle gas stream and the recycle gas stream is admixed with the first feed gas stream, prior to the first catalytic methanation. The second product gas stream is subjected to a carbon dioxide removal process to produce SNG.

14 Claims, 2 Drawing Figures

PRODUCTION OF SUBSTITUTE NATURAL GAS

This invention relates to the production of fuel gases suitable for use as substitute natural gas (SNG) from a primary synthesis gas produced by the partial oxidation of carbonaceous fuels such as oils or coal.

Processes are known whereby liquid or solid fuels may be gasified to give a product containing minor quantities of methane and much larger amounts of hydrogen and carbon monoxide. These gases are unsuitable for use as SNG but can be upgraded by reaction of the carbon monoxide with steam to give carbon dioxide and hydrogen and thereafter this so called shifted gas can be subjected to methanation reactions. Since the catalysts employed for methanation reactions are usually sensitive to sulphur poisoning it has been common practice to place a desulphurisation train prior to the methanation system. Usually carbon dioxide is also removed from the gas at this stage, so that the final gas, after methanation, is substantially methane.

The present invention now proposes a process for upgrading gases such as those produced by the partial oxidation of carbonaceous fuels which dispenses with the necessity of effecting a shift reaction on the gases prior to methanation and wherein the methanation reaction can be performed under adiabatic conditions, which process offers lower capital and operating costs for gas production than hitherto known.

In accordance with the present invention there is provided a process for methanating primary synthesis gases containing carbon monoxide and hydrogen to produce a substitute natural gas which process comprises simultaneously heating and saturating the primary synthesis gas with water, further heating and dividing the synthesis gas into first and second feed gas streams, subjecting the first feed gas stream to a first methane synthesis reaction over a catalyst at a temperature of from 250° to 550° C., mixing the product of the first reaction with said second feed gas stream and effecting a second methane synthesis reaction on said mixture over a second catalyst at a temperature of from 250° to 550° C., dividing the product of the second reaction into a second product gas stream and a recycle gas stream, admixing the recycle gas stream with the first feed gas stream, prior to effecting said first methane synthesis reaction, and subjecting said second product gas stream to a carbon dioxide removal process.

The process of the invention may be carried out at pressures up to about 2000 psig, and typically the pressure may range from 50 to 1000 psig.

According to a modification of the process of the invention, the heated primary synthesis gas may be divided into more than two feed gas streams and subjected to more than two methane synthesis reactions, the first and second feed gas streams being subjected to methanation reactions as described above and, wherein the third feed gas stream is admixed with the second product gas stream and subjected to a third methane synthesis reaction to produce a third product gas stream. Similarly a fourth feed gas stream may be mixed with the third product gas stream and effecting a fourth methane synthesis reaction to produce a fourth product gas stream. Such third and fourth methane synthesis reactions may also be conducted at a temperature of from 250° to 550° C. Any further feed gas streams may be subjected to methanation by mixing with the product gas from the previous methanation stage and subjecting the mixture to subsequent methanation reactions. It may be desirable to recycle a portion of a subsequent product gas stream back to the inlet of one or more earlier methanation stages by mixing said recycled product gas with the product gas stream from the previous methanation stage. Furthermore, it may be desirable to subject the third and subsequent feed gas streams to separate methane synthesis reactions prior to combination with the respective product gas streams. The carbon dioxide removal process may be effected on the product gas stream from the last methanation reaction.

In order to upgrade the gas further the invention further provides for the addition of at least one further methanation unit taking the whole of the product gas stream immediately prior to the carbon dioxide removal step. The further methane synthesis units may be operated under substantially the same operating temperature and pressure ranges as those for the other units. It may be desired to remove some or all of the water vapour from the gas prior to some or all of the methanation stages after the first two in order to adjust the composition of the final gas.

The primary synthesis gas to be treated in accordance with the invention may be any gas produced by oxidation processes. For example, the gases may be produced by the well known partial oxidation routes for heavy oils or by the gasification of coals with steam and oxygen. The process of the invention is suitable for use with primary synthesis gases having very high contents of carbon monoxide, eg of the order of greater than 40% by volume (dry basis) and preferably greater than 50% by volume and low steam contents of, eg less than, 50% by volume(steam/dry gas), such as those produced by high pressure slagging gasifiers. Such gasifiers are described, for example, in UK Patent Specification No. 977,122. The process of the invention is particularly suitable to those synthesis gases having a volumetric steam to carbon monoxide ratio of from 0–1.0:1.0.

Prior to carrying out the methane synthesis reactions the primary synthesis gases are saturated with water. Typically the temperature of the water is about 180° to 200° C., but the temperature may vary from 150° to 300° C. After saturation the gas may have a steam to dry gas ratio (v/v) of from 0.1–1.0:1.0.

The water used in the saturator is preferably heated by heat exchange with cooling gas streams within the plant. For example, heat may be raised by indirect heat exchange with primary synthesis gas prior to desulphurisation and/or with the final methanated product gas prior to the final carbon dioxide removal stage. However, the heat available from these sources is generally only available at relatively low temperatures and it may be insufficient to raise the temperature of the saturator water to that desired. The desired temperature may be obtained by contacting at least a portion of the saturator water stream with a source from which heat is available at high temperatures. Thus, at least part of the saturator water stream may be subjected to indirect heat exchange with a source of high grade heat within the process, for example, with the first methane synthesis state product, either before or after admixture of said first stage product with the second stream of saturated primary synthesis gas.

Since water is consumed during the methane synthesis reactions and a further part may be lost as a purge stream in the removal of contaminants which build-up in the saturator liquor system, a water make-up stream is necessary. This make-up stream may be heated by indirect heat exchange with cooling gas streams prior to admixture with excess unevaporated water recovered from the saturator for further use.

Most of the remaining heat which needs to be removed from the gas streams within the process is available at relatively high temperatures and this allows high pressure steam to be generated for use in other parts of the gasification process, for example, within the primary synthesis gas producer or for the generation of mechanical power.

The efficiency of the process is maximised by not effecting the methane synthesis in a single stage. Because of the nature of the catalysts it is necessary to control the maximum temperatures obtained in each reactor and this is achieved by recirculating at least part of the methanated gas product, and by by-passing a part of the saturated primary synthesis gas around at least the first stage. Higher steam contents and higher recirculating ratios effect the efficiency of the process, and they are minimised within the constraints of avoiding excessive reactor temperatures and carbon depositions in the catalyst (by mechanisms such as the Boudouard Reaction). A further advantage of dividing the feed gas between the first and second stages is that it readily allows a closer control of reaction temperatures and the use of smaller amounts of recycle gas. The amount of gas recycled is defined by the recycle ratio. The recycle ratio is expressed by the relationship —

$$\text{Recycle Ratio} = \frac{\text{Amount of Gas Recycled}}{\text{Amount of Gas Passing to Next Stage}}$$

The process of the invention may be carried out using recycle ratios of from 0.2 to 10:1.0 preferably from 1.0 to 6.0:1.0.

According to the various embodiments of the invention gases may be recycled at several positions. We have found that the recycle ratios for each stage may be smaller, the larger the number of stages employed. For methanators operating under substantially similar conditions, there is generally an inverse linear relationship between the recycle ratio (for a given stage) and the number of reactors or stages.

The gas leaving the final methane synthesis stage has a carbon dioxide content which can be above 50% by volume rendering it unsuitable as SNG. It is therefore necessary to treat this gas to lower the carbon dioxide content to less than 10%, eg about 2%. In many cases conventional physical and chemical absorption systems may be employed. However, since the final methane synthesis product gases are likely to have a very high partial pressure of carbon dioxide it has been found especially advantageous to employ cryogenic techniques to remove the bulk of the carbon dioxide. Whatever process is employed for carbon dioxide removal the process of the invention has the advantage that the high partial pressure of carbon dioxide allows more efficient carbon dioxide removal. The conditions under which the methanation stages operate mean that the carbon monoxide and hydrogen content can be controlled more easily than hitherto. If physical absoroption processes such as the Rectisol, Selexol or Sulfinol processes are employed it has been observed that further drying of the gas to pipeline specification is not unually necessary.

The processes employed for carbon dioxide removal may also be employed for the removal of impurities such as hydrogen sulphide and carbonyl sulphide prior to effecting the methane synthesis reactions in accordance with the invention.

It is advantageous to employ the same process to treat the gas streams before and after the methane synthesis stages since such integration leads to lower costs and lower energy requirements for absorbent regeneration purposes.

The removal of sulphur compounds from the primary synthesis gas is easier since the stripped gas from the regenerator of the absorption process will have a much higher hydrogen sulphide content than that obtained if the gas is so treated after being subjected to a conventional shift reaction and this will greatly aid sulphur production.

Chemical absorption processes might be best for the final $CO_2$ removal stage since a physical absorption process, such as the Rectirol Process, would have methane loss problems, but we are unaware of the extent of this problem here, where, presumably, the absorption and stripping stages will not have to operate under conditions as severe as those encountered when both sulphur compounds and $CO_2$ are to be removed.

Since the catalysts used for the methane synthesis reactions are usually extremely sensitive to poisoning by sulphur compounds, if the gas purification stage prior to the saturation stage does not remove sulphur compounds to a sufficiently low level, it is necessary to perform a further fine purification stage. If such a fine purification process is required to operate at high temperatures, eg absorption by zinc oxide containing materials, it is best performed after saturation of the primary synthesis gas, eg upon steam-containing gases, provided that the presence of steam in the gas does not adversely effect the operation of the purification process.

The reasons for the higher efficiency for the process of the invention are not believed to be self evident. It can be looked upon as resulting from the reduced number of main stream cooling steps, in that, the cooling of the water laden shifted gas, which in any event would yield mostly heat at low temperature, is eliminated. Equally it can be seen as the liberation of heat, mainly in the methane synthesis stages which is suitable for high pressure steam generation at a useful temperature, whilst high pressure steam has to be added to a conventional shift stage. In a sense, in the methane synthesis stages, the steam for the shift reactions is in part generated internally by the concurrent methanation reactions which also consume the hydrogen produced in the shift reactions.

The obtaining of a high efficiency is dependent on the transfer of low grade heat from the primary synthesis gas, prior to purification, and final methanated gas to the purified synthesis gas to be subjected to the process of the invention The stream to the methane synthesis stages contains much high grade heat because of the relatively high temperature and high steam content. It is advantageous to raise this steam at its partial pressure in this gas as opposed to the full pressure of the system, as would be necessary if this were raised in a boiler and added as high pressure steam. This is achieved by the use of the saturator. Corrosion problems with saturated carbon monoxide containing gases have been evidenced both at low and high temperatures. However, at temperatures in the range of 150° C. to 250° C. no corrosion problems have been experienced, even after considerable use.

Generally since the methane synthesis reactions are accompanied by a significant decrease in gas volume, compared with conventional shift reactions, it is not usually advantageous to cool by direct contact with cold water to obtain the heat exchange from the final methanated gas.

Figure 2:
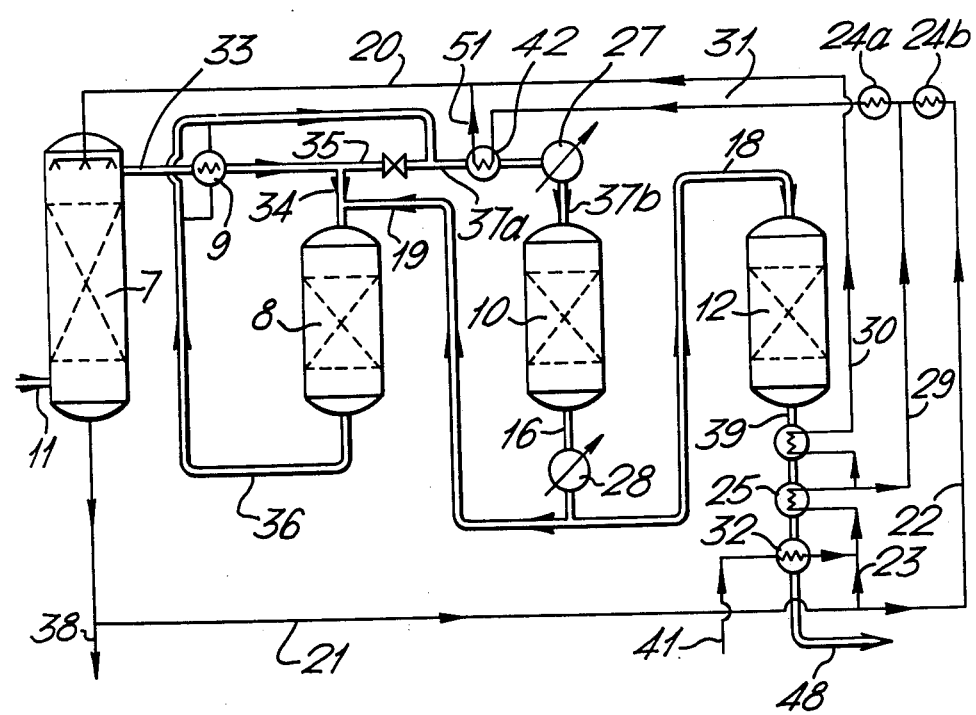

The invention will now be described with reference to the accompanying drawings, in which:

FIG. 1 is a schematic representation of a gas making plant employing the process of this invention; and FIG. 2 is a schematic representation of part of FIG. 1 showing an alternative arrangement for heating the saturator water stream.

Apparatus common to both figures are designated by the same numeral.

Referring to FIG. 1, a primary synthesis gas is produced in a slagging gasifier 1. The synthesis gas is first treated and cooled to remove tars and oils therefrom in separators exchangers 2, 40 and 3 respectively. The tar and oil free gas is then subjected to desulphurisation in unit 5. In the embodiment shown the sour gas 24 is first subjected to a naphtha pre-washing unit 4 prior to absorption in 5. With some kinds of desulphurisation processes pre-washing is not necessary. The desulphurisation process can be effected at relatively low temperatures and, thus, the sour gas 24 is heat exchanged with the sweet gas 11 in heat exchanger 6 to maximise thermal efficiency. Sweet gas 11 is then saturated with water in saturator 7, water being provided by line 20 and the unevaporated water removed via line 21. Stream 33 is then divided into two streams 34 and 35. Gas stream 34 is then subjected to a first methane synthesis reaction in vessel 8 and the product gas 36 cooled by heat exchange with stream 33 in exchanger 9. Cooled stream 36 is combined with stream 35 to produce a mixed stream 15 which, after temperature adjustment, is subjected to a second methane synthesis reaction in vessel 10 to produce gas stream 16. Stream 16 is divided into two streams, recycle stream 19 which is combined with stream 34 as the feestream for reactor 8 and stream 18 which is reacted in a third methane synthesis reactor 12 to produce gas stream 39. The final product stream 39, after cooling in heat exchanger 14, is treated to remove carbon dioxide in vessel 13 to give an SNG 48.

The water stream 21 recovered from the saturator 7 is recycled via pump 43 for further heating and re-use. In the embodiment shown, stream 21 is divided into streams 22 and 23. Stream 22 is heated by heat exchange with the primary synthesis gas in exchanger 24 and recombined with stream 23 after heat exchanger 25 which is further heated by heat exchange with the final product gas 39 in exchanger 26 to form stream 20 which passes to saturator 7. The water loop formed by streams 21, 22, 23 and 20 is also provided with inlets and take-off points (not shown) for adding make-up water and removing a purge stream respectively.

High pressure steam boilers are provided at 27 and 28 to utilise the high grade heat available in the cooling gas streams 15 and 16 respectively.

Referring to FIG. 2, water stream 21 is divided again to form two streams 22 and 23. Stream 22, as shown in FIG. 1, is heated by synthesis gas in exchanger 24b. Stream 23 is admixed with make-up water 41 heated by stream 39 in exchanger 32 and the combined stream heated by exchanger 25. This stream is divided into streams 29 and 30, stream 29 combining with stream 22 and passing through exchanger 24a, which cools crude primary synthesis gas, before forming stream 31. Water stream 31 is then subjected to heat exchange with a high grade heat source in exchanger 42. Stream 30 is combined with the very hot stream 51 to form stream 20, which passes to saturator 7. Purge liquors may be removed from the water loop via line 38.

The invention will now be illustrated by the following Examples.

EXAMPLE 1

Apparatus as shown in FIG. 1 was employed to produce SNG having the characteristics shown in Table 1, stream No. 48. The stream numbers shown in Table 1 report the gas characteristics of the gas at various stages in its production as shown by the same numerals in FIG. 1 of the drawings.

The recycle ratio Volume of Gas 19/Volume of Gas 18 was 2.59.

TABLE 1

| STREAM NO. | 1 | 24 | 11 | 33 | 15 | 37 | 16 | 19 | 34 | 36 | 18 | 39 | 48 |
|---|---|---|---|---|---|---|---|---|---|---|---|---|---|
| Press. (psia) | 465 | 430 | 405 | 390 | 373 | 370 | 355 | 387 | 375 | 373 | 350 | 335 | 1000 |
| Temp (° C) | 632 | 32 | 30 | 177 | 418 | 280 | 462 | 280 | 280 | 462 | 280 | 320 | 30 |
| COMPONENT | | | | | | | | | | | | | |
| Co lb mol/h | 61.48 | 61.48 | 61.48 | 61.48 | 35.66 | 35.66 | 2.59 | 1.87 | 27.94 | 2.12 | 0.72 | 0.03 | 0.03 |
| $CO_2$ lb mol/h | 1.34 | 1.34 | 1.00 | 1.00 | 126.98 | 126.98 | 149.12 | 107.58 | 0.45 | 126.43 | 41.55 | 41.32 | 0.33 |
| $H_2$ lb mol/h | 24.74 | 24.74 | 24.74 | 24.74 | 24.17 | 24.17 | 13.00 | 9.38 | 11.24 | 10.68 | 3.62 | 0.63 | 0.63 |
| $CH_4$ lb mol/h | 8.49 | 8.49 | 8.49 | 8.49 | 96.39 | 96.39 | 108.06 | 77.97 | 3.86 | 91.75 | 30.11 | 31.03 | 31.03 |
| $C_2H_6$ lb mol/h | 0.41 | 0.41 | 0.41 | 0.41 | 0.23 | 0.23 | — | — | 0.19 | — | — | — | — |
| $C_2H_4$ lb mol/h | 0.27 | 0.27 | 0.27 | 0.27 | 0.15 | 0.15 | — | — | 0.12 | — | — | — | — |
| $N_2$ lb mol/h | 0.69 | 0.69 | 0.69 | 0.69 | 2.49 | 2.49 | 2.49 | 1.80 | 0.32 | 2.11 | 0.69 | 0.69 | 0.69 |
| $H_2 S$ lb mol/h | 2.19 | 2.19 | — | — | — | — | — | — | — | — | — | — | — |
| Steam lb mol/h | 16.14 | 0.16 | — | 51.79 | 124.10 | 124.10 | 112.89 | 81.41 | 23.54 | 95.85 | 31.46 | 32.60 | — |
| Tars lb/hr | 151.23 | — | — | — | — | — | — | — | — | — | — | — | — |
| Oils lb/hr | 15.20 | — | — | — | — | — | — | — | — | — | — | — | — |
| Naphtha lb/hr | 38.30 | 38.30 | — | — | — | — | — | — | — | — | — | — | — |
| $NH_3$ lb/hr | 11.0 | — | — | — | — | — | — | — | — | — | — | — | — |
| Fatty acids lb/hr | 4.48 | — | — | — | — | — | — | — | — | — | — | — | — |

EXAMPLE 2

The apparatus of FIG. 1 was modified, as shown in FIG. 2, and an SNG prepared under the conditions set out in Table 2. As in Example 1, the stream number reports the gas characteristics at similarly designated points in FIG. 2.

The recycle ratio Volume of Gas 19/Volume of Gas 18 was 2.59.

TABLE 2

| STREAM NO. | 1 | 33 | 15 | 37 | 16 | 19 | 34 | 36 | 18 | 39 |
|---|---|---|---|---|---|---|---|---|---|---|
| Hydrogen, lb m/h | 21988 | 21988 | 21484 | 21484 | 11556 | 8335 | 9993 | 9489 | 3220 | 560 |
| Methane, lb m/h | 7555 | 7555 | 85677 | 85677 | 96055 | 69302 | 3433 | 81556 | 26765 | 27584 |
| Carbon monoxide, lb m/h | 54653 | 54653 | 31696 | 31696 | 2305 | 1663 | 24839 | 1882 | 642 | 24 |

TABLE 2-continued

| STREAM NO. | 1 | 33 | 15 | 37 | 16 | 19 | 34 | 36 | 18 | 39 |
|---|---|---|---|---|---|---|---|---|---|---|
| Carbon dioxide, lb m/h | 889 | 889 | 112868 | 112868 | 132545 | 95627 | 404 | 112384 | 36933 | 36731 |
| Nitrogen, lb m/h | 617 | 617 | 2215 | 2215 | 2215 | 1598 | 280 | 1878 | 617 | 617 |
| Ethane, lb m/h | 367 | 367 | 200 | 200 | — | — | 167 | — | — | — |
| Ethylene, lb m/h | 241 | 241 | 131 | 131 | — | — | 109 | — | — | — |
| Tot. gas dry, lb m/h | 86310 | 86310 | 254271 | 254271 | 244676 | 176525 | 39225 | 207189 | 68177 | 65516 |
| Steam, lb m/h | — | 46034 | 110312 | 110312 | 100348 | 72361 | 20922 | 85199 | 27961 | 28982 |
| Tot. Gas wet, lb m/h | 86310 | 132344 | 364583 | 364583 | 345024 | 248886 | 60147 | 292388 | 96138 | 94498 |
| Temperature, °F | 86 | 351 | 761 | 536 | 864 | 536 | 536 | 863 | 536 | 608 |
| Press, psig | 390 | 375 | 360 | 355 | 340 | 372 | 372 | 360 | 335 | 320 |

The final gas had the composition shown in the column headed 39 in Table 2.

We claim:

1. A process for producing a methane containing substitute natural gas from a primary synthesis gas containing more than 40 percent by volume of carbon monoxide on a dry basis and hydrogen comprising the steps of:
simultaneously heating and saturating said primary synthesis gas with water;
heating the saturated synthesis gas further and dividing the same into first and second feed gas streams;
admixing a recycle gas stream from the product gas of second concurrent shift and methanation reactions with the first feed gas stream and subjecting the admixture to first concurrent shift and methanation reactions over a catalyst at a temperature of from 250° to 550° C.;
mixing the product of the first reactions with said second feed gas stream and effecting second concurrent shift and methanation reactions on said mixture over a second catalyst at a temperature of from 250° to 550° C.;
dividing the product of the second reactions into a second product gas stream and said recycle gas stream; and
subjecting said second product gas stream to a carbon dioxide removal process.

2. A process as claimed in claim 1, wherein said primary synthesis gas contains greater than 50% by volume (on a dry basis) of carbon monoxide.

3. A process as claimed in claim 1, wherein the saturated primary synthesis gas also contains steam in a ratio of up to 1 part by volume of steam per 1 part by volume of the dry gas.

4. A process as claimed in claim 1, wherein the synthesis gas, after said saturation, has a steam to dry gas ratio (on a volume basis) of 0.1–1.0:1.0.

5. A process as claimed in claim 1, wherein the process is carried out at a pressure of from 50 to 2000 psig.

6. A process as claimed in claim 1, wherein the volumetric ratio of recycle gas stream to second product gas stream is from 1.0–6.0:1.0.

7. A process as claimed in claim 1, wherein the heated synthesis gas is divided into three feed gas streams, said third feed stream being combined with said second product gas and subjected to a third methanation reaction at a temperature of from 250° to 550° C. to produce a third product gas stream.

8. A process as claimed in claim 7, wherein the heated synthesis gas is divided into four feed gas streams, said fourth feed stream being combined with said third product gas stream and subjected to a fourth methanation reaction at a temperature of from 250° to 550° C. to produce a fourth product gas stream.

9. A process as claimed in claim 7, wherein a portion of said third product stream is recycled back to at least one of the inlets of said first, second and third methanation stages.

10. A process as claimed in claim 1, wherein said second product gas stream is subjected to a further catalytic methanation prior to carbon dioxide removal.

11. A process as claimed in claim 10, wherein water vapour is removed from the second product gas stream prior to said further catalytic methanation.

12. A process as claimed in claim 1, wherein the temperature of the water added to saturate the primary synthesis gas is from 150° to 300° C.

13. A process as claimed in claim 12, wherein at least a portion of said water is heated by indirect heat exchange with the product of the first methanation reaction.

14. A process as claimed in claim 13, wherein said water is heated by indirect heat exchange with the product of the first methanation reaction after admixture of said product with said second stream.

* * * * *